(12) United States Patent
Obel et al.

(10) Patent No.: US 6,912,422 B1
(45) Date of Patent: Jun. 28, 2005

(54) IMPLANTABLE DUAL CHAMBER HEART STIMULATOR

(75) Inventors: Martin Obel, Danderyd (SE); Berit Larsson, Danderyd (SE)

(73) Assignee: St. Jude Medical AB, Jaerfaella (SE)

( * ) Notice: Subject to any disclaimer, the term of this patent is extended or adjusted under 35 U.S.C. 154(b) by 609 days.

(21) Appl. No.: 10/111,907

(22) PCT Filed: Oct. 3, 2000

(86) PCT No.: PCT/SE00/01903

§ 371 (c)(1),
(2), (4) Date: Apr. 26, 2002

(87) PCT Pub. No.: WO01/30443

PCT Pub. Date: May 3, 2001

(30) Foreign Application Priority Data

Oct. 26, 1999  (SE) ............................... 9903867

(51) Int. Cl.[7] .............................................. A61N 1/362
(52) U.S. Cl. ...................................................... 607/28
(58) Field of Search ............................... 607/9, 27, 28

(56) References Cited

U.S. PATENT DOCUMENTS

| | | | |
|---|---|---|---|
| 5,476,487 A | 12/1995 | Sholder | 607/28 |
| 5,766,229 A | 6/1998 | Bornzin | 607/28 |
| 6,047,213 A * | 4/2000 | Sirokman et al. | 607/9 |
| 6,115,632 A * | 9/2000 | Akers et al. | 607/9 |

FOREIGN PATENT DOCUMENTS

| | | | | |
|---|---|---|---|---|
| EP | 0 850 662 A2 * | 1/1998 | | A61N/1/37 |
| WO | WO 95/24944 | 9/1995 | | A61N/1/365 |
| WO | WO 96/04956 | 2/1996 | | A61N/1/365 |

* cited by examiner

*Primary Examiner*—Carl H. Layno
(74) *Attorney, Agent, or Firm*—Schiff Hardin LLP

(57) ABSTRACT

The invention relates to an implantable dual chamber heart stimulator comprising a stimulation threshold detector arranged to activate a stimulation threshold search algorithm to perform a stimulation threshold search at predetermined time intervals in order to determine a stimulation threshold of heart tissue. The heart stimulator comprises an AV-interval generator adapted to generate an AV-interval and a controller arranged to temporarily shorten the AV-interval to a threshold search AV-interval when this threshold search is performed. The heart stimulator further comprises AR/PR-interval measure adapted to measure the actual AR/PR conduction time in which this threshold search AV-interval is set by the AV-interval generator and the controller to the measured AR/PR-interval shortened by a predetermined time.

9 Claims, 2 Drawing Sheets

IMPLANTABLE DUAL CHAMBER HEART STIMULATOR

BACKGROUND OF THE INVENTION

1. Technical Field of the Invention

The present invention relates to an implantable dual chamber heart stimulator comprising a stimulation threshold detector, an AV-interval generator, and a controller.

2. Description of the Related Art

To reduce the energy consumption of heart stimulators, an automatic threshold search function is used to maintain the energy of the stimulation pulses at a level just above that which is needed to effectuate capture.

FIG. 1 discloses an intracardiac electrogram (IEGM) illustrating the principles of threshold search algorithms according to established standard prior art (see e.g., U.S. Pat. No. 5,476,487) and which principles the present invention addresses. FIG. 1 shows atrial A and ventricular V stimulation pulses, as well as a high output backup pulse BU delivered if loss of capture (LOC) occurs. As can be seen in complex 3, the pre-programmed AV-interval is prolonged with an atrial pulse A when an LOC occurs (complex 2). The reason for that is to wait for any intrinsic event if the first LOC was the result of a fusion beat. In this case there is no intrinsic activity and the LOC was not a result of a fusion beat but was due to a changed stimulation threshold of the heart tissue, and a stimulation threshold search is initiated. During the threshold search, the pre programmed AV-interval is shortened to "'AV-short" to override any intrinsic heart activity. The ventricular stimulation amplitude is successively stepped up by a predetermined amplitude step of, e.g. 0.1–0.3 V, and each unsuccessful ventricular stimulation pulse is followed by a back-up pulse. As an alternative, the ventricular stimulation amplitude may start at an amplitude above the stimulation threshold and then successively be stepped down until non capture occurs. This is performed until the stimulation threshold is detected, i.e. capture is detected from the ventricular stimulation pulse, and the stimulation pulse amplitude is then set to a value that equals the stimulation threshold plus a working margin, e.g. 0.3 V.

For the purposes of the discussions and definitions below relating to the invention, the present invention is directed to a dual chamber heart stimulator having, among other things, an inhibiting function such that, using the commonly accepted terminology, the AV interval could also be started by an intrinsic atrial heart activity (a P-wave), and the started interval is then designated a PV interval. Thus, instead of using the nomenclature "PV/AV-interval" to describe this, the nomenclature "AV-interval" or "AVI" is used in this application whenever there is no need to distinguish between the two. The AVI so far discussed is thus artificial in the sense that it is controlled by an AV-counter in the pacemaker. However, there is also a natural AV interval or AV conduction time, which is related to the physiological conduction pathway in the heart. This interval is also referred to as the PR/AR interval as it starts with either a P-wave or an A-pulse and ends with the natural ventricular depolarization indicated by an R-wave. Whenever necessary for clarity, the more specific terms just discussed will be used.

U.S. Pat. No. 5,766,229 discloses another capture verification method and apparatus for a single chamber or a double chamber implantable pacemaker utilizing heart rhythm stability measurements to minimize the likelihood of fusion.

SUMMARY OF THE INVENTION

It is an object of the present invention to provide an improved dual chamber heart stimulator with a dynamic determination of the AV-interval adapted for stimulation threshold searches.

According to the invention is the above-mentioned improvement achieved by an implantable dual chamber heart stimulator, comprising a stimulation threshold detector arranged to activate a stimulation threshold search algorithm to perform a stimulation threshold search at predetermined time intervals in order to determine a stimulation threshold of heart tissue; an AV-interval generator adapted to generate an AV-interval; a controller arranged to temporarily shorten said AV-interval to a threshold search AV-interval when said threshold search is performed; and an AR/PR-interval measurer adapted to measure an actual AR/PR conduction time, said threshold search AV-interval being set by the AV-interval generator and the controller to the measured AR/PR-interval shortened by a predetermined time. The invention is also achieved by a method of using the implantable dual chamber heart stimulator.

The inventive dual chamber heart stimulator thus performs threshold searches using an AVI that achieves good hemodynamic of the heart and that avoids fusion. The present invention is especially applicable when the threshold search is activated at predetermined time intervals due to the fact that the hemodynamic situation of the heart at this time is more stable compared to threshold searches activated due to loss of capture.

DETAILED DESCRIPTION OF PREFERRED EMBODIMENTS OF THE INVENTION

Figure 1:
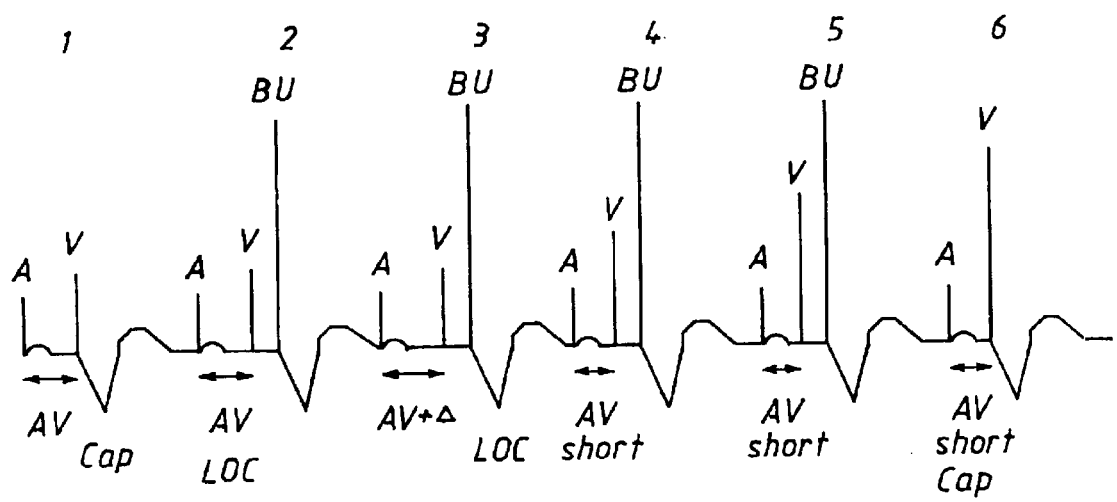
FIG. 1 is a timing diagram of an IEGM illustrating a threshold search algorithm applicable in relation to the present invention.
Figure 2:
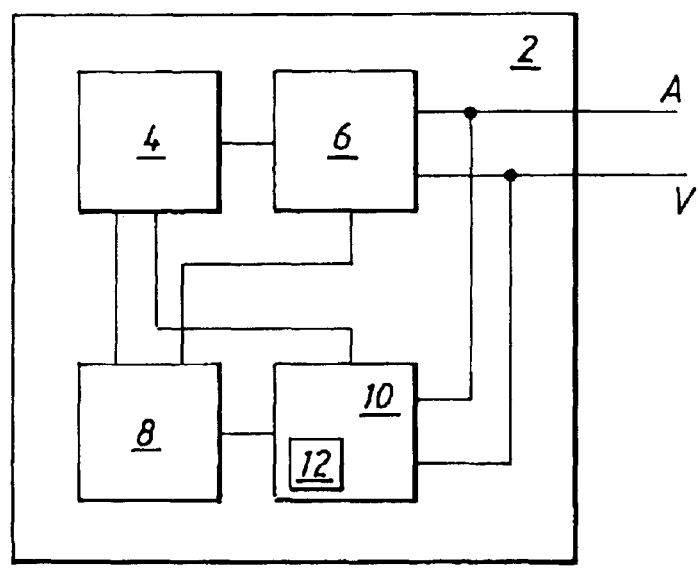
FIG. 2 is a schematic block diagram of an implantable heart stimulator according to the present invention.

FIG. 2 is a schematic block diagram of an implantable dual chamber heart stimulator 2 according to the present invention. The heart stimulator is adapted to be connected to heart electrode leads that in turn are adapted to be inserted into the atrium and into the ventricle of the heart in accordance with established implantation techniques. The heart stimulator comprises an AV interval generator 4, a stimulation pulse generator 6, a controller 8 and a stimulation threshold detector 10 including an AR/PR interval measurer 12.

A stimulation threshold search algorithm, preferably in accordance with the algorithm described above, stored in the controller 8 is activated at predetermined time intervals, e.g. every 8 hours. When the algorithm is activated, the AVI is shortened in order to override intrinsic activity.

The programmed AVI is initially set to a value of about 160 ms ("shipped setting"). Some implantable heart stimulators have different values for AVI and PVI (interval started by intrinsic atrial activity, a P-wave) where AVI is longer than PVI; typical values are 170 ms for AVI and 150 ms for PVI. The reason for having different values is to even out the differences in pumping capacity during stimulation and inhibition, respectively. The difference in the duration of these two intervals is referred to as "hysteresis".

As described above the AVI is shortened to AV short during a stimulation threshold search according to a threshold search algorithm in order to override any intrinsic activity.

According to one alternative of a prior art threshold search algorithm is that AV short is 25 ms or 50 ms, depending on whether the atrial activity was intrinsic (PVI) or stimulated (AVI), respectively. According to another alternative, the programmed AVI is shortened by a predetermined time, e.g., between 30–50 ms.

According to the present invention, the PR/AR conduction time measured. That time is then shortened with a predetermined time to obtain a threshold search AVI. The predetermined time by which the measured time is shortened is 30–50 ms, preferably 40 ms. The PR/AR conduction time measurement is performed in the following way. The PVI/AVI is temporarily prolonged to typically 180/200 ms, respectively, during a small number of heart cycles, typically in the order of five. If, during this time, it was possible to measure the conduction time, then the measured conduction time is used for performing the threshold search as described above. If the conduction time was measured, but the resulting threshold search AVI was shorter than a threshold search AVI limit, then the threshold search is preferably postponed and the conduction measurement is repeated at regular intervals until a conduction time is measured that allows a threshold search to be performed. The threshold search AVI limit is preferably in the range of 80–120 ms, typically 100 ms, but other values are also possible. If a threshold search is postponed due to the fact that the conduction time is too short, then there is no need for ventricular pacing (due to the fact that there is intrinsic ventricular activity present), so there is no drawback to postponing the threshold search under these conditions.

Figure 3:
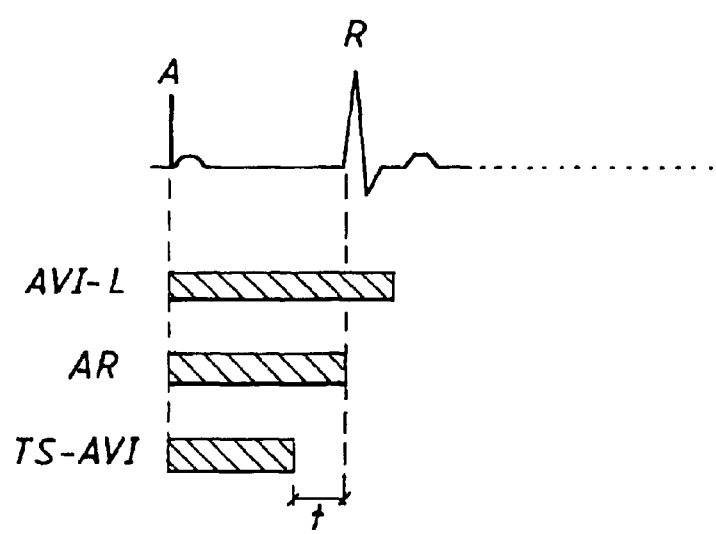
FIG. 3 is a timing diagram of an IEGM showing a part of a heart cycle illustrating the principles of the present invention.

Another possibility is that it is not possible to measure the conduction time, e.g., due to conduction failures, e.g., AV-blocks. In that case, the programmed AVI shortened with a predetermined value is used and checked against the threshold search AVI limit as described above. The PR/AR interval conduction time measurements are performed by the PR/AR interval conduction time measurer 12 in conjunction with the AVI generator 4. The evaluation of the result of the measurements are performed by the controller 8. FIG. 3 shows an IEGM that illustrates a part of a heart cycle using the principles of the present invention.

FIG. 3 shows a prolonged AVI (AVI-L) started when an atrial stimulation pulse A is applied. Intrinsic ventricular activity R that occurs during the prolonged AVI is detected and the actual AR conduction time (AR) is measured by the AR/PR-interval measurer 12. When a threshold search then is then performed is based on a threshold search AVI (TS-AVI) set by the AV-interval generator 4 and the controller 8 to the measured AR shortened by a predetermined time (t).

Many different types of threshold searches are possible.

According to a preferred threshold search, as described above, the search will start at the present ventricular stimulation amplitude with two stimuli and then the amplitude will be decreased for the following two stimuli and so on until a loss of capture is found. When a loss is found, the amplitude is increased for two stimuli. If these stimuli result in capture, then the stimulation threshold is found. A working margin might be added to the threshold to obtain the ventricular stimulation amplitude in accordance with established techniques.

However, the threshold search AVI determined according to the present invention is applicable to any threshold search algorithm.

The present invention is not limited to the above-described preferred embodiments. Various alternatives, modifications and equivalents may be used. Therefore, the above embodiments should not be taken as limiting the scope of the invention. For the purposes of promoting an understanding of the principles of the invention, reference has been made to the preferred embodiments illustrated in the drawings, and specific language has been used to describe these embodiments. However, no limitation of the scope of the invention is intended by this specific language, and the invention should be construed to encompass all embodiments that would normally occur to one of ordinary skill in the art.

The present invention may be described in terms of functional block components and various processing steps. Such functional blocks may be realized by any number of hardware and/or software components configured to perform the specified functions. For example, the present invention may employ various integrated circuit components, e.g., memory elements, processing elements, logic elements, look-up tables, and the like, which may carry out a variety of functions under the control of one or more microprocessors or other control devices. Similarly, where the elements of the present invention are implemented using software programming or software elements the invention may be implemented with any programming or scripting language such as C, C++, Java, assembler, or the like, with the various algorithms being implemented with any combination of data structures, objects, processes, routines or other programming elements. Furthermore, the present invention could employ any number of conventional techniques for electronics configuration, signal processing and/or control, data processing and the like.

The particular implementations shown and described herein are illustrative examples of the invention and are not intended to otherwise limit the scope of the invention in any way. For the sake of brevity, conventional electronics, control systems, software development and other functional aspects of the systems (and components of the individual operating components of the systems) may not be described in detail. Furthermore, the connecting lines, or connectors shown in the various figures presented are intended to represent exemplary functional relationships and/or physical or logical couplings between the various elements. It should be noted that many alternative or additional functional relationships, physical connections or logical connections may be present in a practical device. Moreover, no item or component is essential to the practice of the invention unless the element is specifically described as "essential" or "critical". Numerous modifications and adaptations will be readily apparent to those skilled in this art without departing from the spirit and scope of the present invention.

What is claimed is:

1. An implantable dual chamber heart stimulator, comprising:
   a stimulation threshold detector arranged to activate a stimulation threshold search algorithm to perform a stimulation threshold search at predetermined time intervals in order to determine a stimulation threshold of heart tissue;
   an AV-interval generator adapted to generate an AV-interval;
   a controller arranged to temporarily shorten said AV-interval to a threshold search AV-interval when said threshold search is performed; and
   an AR/PR-interval measurer adapted to measure an actual AR/PR conduction time, said threshold search AV-interval being set by the AV-interval generator and the controller to the measured AR/PR-interval shortened by a predetermined time.

2. The heart stimulator according to claim 1, wherein said controller is configured to set said predetermined time to 30–50 ms.

3. The heart stimulator according to claim 1, wherein said AV-interval generator is configured to temporarily prolong said AV-interval a predetermined number of heart cycles in order to perform said measurement of said actual AR/PR conduction time using said controller.

4. The heart stimulator according to claim 3, wherein said AV-interval generator is configured to prolong said AV-interval to 180–200 ms.

5. The heart stimulator according to claim 3, wherein said predetermined number of heart cycles is 4–7.

6. The heart stimulator according to claim 1, further comprising:
   a predetermined permanently programmed AV-interval utilized by said AV-interval generator.

7. The heart stimulator according to claim 2, wherein said controller is configured to set said predetermined time to 40 ms.

8. The heart stimulator according to claim 3, wherein said predetermined number of heart cycles is 5.

9. A method for operating an implantable dual chamber heart stimulator, comprising:

activating a stimulation threshold search algorithm;

perform a stimulation threshold search at predetermined time intervals based on said activating;

determining a stimulation threshold of heart tissue based on said simulation threshold search;

generating an AV-interval by an AV-interval generator;

measuring an actual AR/PR conduction time with an AR/PR-interval measurer;

temporarily shortening said AV interval to a threshold search interval by a controller when said stimulation threshold search is performed, said threshold search AV-interval being set by the AV-interval generator and the controller to the measured AR/PR-interval shortened by a predetermined time.

* * * * *